United States Patent [19]

Hefton

[11] Patent Number: 5,000,963

[45] Date of Patent: Mar. 19, 1991

[54] METHOD OF TREATING THE SKIN USING HUMAN EPIDERMAL SHEETS

[76] Inventor: John M. Hefton, #1 Fifth Ave., New York, N.Y. 10003

[21] Appl. No.: 203,961

[22] Filed: Jun. 8, 1988

Related U.S. Application Data

[62] Division of Ser. No. 504,190, Jun. 14, 1983, Pat. No. 4,769,317.

[51] Int. Cl.$^5$ ............... A61K 35/36; A61F 2/10; C12N 5/00
[52] U.S. Cl. ............... 424/574; 623/15; 435/1; 435/240.2; 435/240.21; 435/240.23; 435/240.25; 435/240.31; 435/268; 435/270

[58] Field of Search ............ 424/95, 520; 623/15; 435/1, 240.2, 240.21, 240.23, 240.25, 240.31, 268, 270

[56] References Cited

U.S. PATENT DOCUMENTS 4,299,819 11/1981 Eisinger ............... 424/95
4,304,866 12/1981 Green et al. ............... 623/15

Primary Examiner—Jacqueline Stone
Assistant Examiner—Jean Witz
Attorney, Agent, or Firm—Sughrue, Mion, Zinn, Macpeak & Seas

[57] ABSTRACT

Procedures are disclosed for eliminating immune competent cells from a population of human epidermal cells. The cells free of immune competent cells are used for growing tissue sheets suitable for transplantation to recipients unrelated to the donor.

10 Claims, No Drawings

METHOD OF TREATING THE SKIN USING HUMAN EPIDERMAL SHEETS

This is a Division of application Ser. No. 504,190 filed June 14, 1983.

BACKGROUND OF THE INVENTION

The present invention relates to the growth of human epidermal cells to produce useful sheet-like products, the resultant products, and use thereof, for example, as skin graft materials.

More particularly, the present invention, and certain of its process embodiments, relate in part to the dissociation of epidermis into epidermal cells and the growth of the epidermal cells into a layer of epidermis consisting essentially of epidermal cells which do not express immune stimulatory antigens. Another aspect of the present invention involves sheet-like products comprising at least one layer of epidermis grown in culture and consisting essentially of non-immune-competent epidermal cells and the use thereof as a skin grafting material.

Previously, the present inventor and a co-worker at that time jointly developed a process for growing human epidermal cells to form an epidermal sheet. See U.S. No. 4,254,226, naming Eisinger and Hefton as co-inventors. U.S. No. 4,254,226 was filed as a continuation application of subsequently abandoned parent application Ser. No. 749. U.S. No. 4,299,819, naming Eisinger as sole inventor and claiming the use of the Eisinger and Hefton epidermal sheet in the treatment of burn victims, was filed as a divisional application of Ser. No. 749. Work related to the Eisinger and Hefton process and epidermal sheet product is found described in Eisinger et al, "Human Epidermal Cell Cultures: Growth and Differentiation in the Absence of Dermal Components or Medium Supplements," *Proc. Natl. Acad. Sci. USA*, volume 76, No. 10, pp. 5340–5344 (Oct., 1979). Also, see Eisinger et al, "Wound Coverage by a Sheet of Epidermal Cells Grown In Vitro from Dispersed Single Cell Preparations," *Surgery, St. Louis*, Volume 88, No. 2, pp. 287–293 (Aug., 1980).

The above described prior art process of Eisinger and Hefton may be summarized as broadly involving the sequence of separating the epidermis in human skin from the dermis, dissociating the epidermis into epidermal cells and growing the epidermal cells in a tissue culture medium. Specific process conditions are disclosed by Eisinger et al for use in each of the above steps and certain of these process conditions will be discussed in greater detail hereinbelow in relationship to a corresponding process step in the cell growth process embodiments of the present invention.

Although there are a number of prior art processes, such as that of Eisinger and Hefton, for growing epidermal cells, to a significant extent the resultant products have been rejected when used as a skin graft for a recipient unrelated to the precursor cell donor, the reason being the rejection of the skin graft cells by the recipient because of the presence of transplantation immunogens on sub-populations of the human epidermal cells of the grown tissue. The transplantation immunogens are present on the Langerhans cells and other cell sub-populations, the latter probably being dendritic epidermal cells. In the above-cited reference, Eisinger 1979 *Proc. Natl. Acad. Sci.* article, ATPase staining was used as an analytical tool to determine the presence of immune-competent Langerhans cells, which are included in the cells carrying surface antigens which cause transplantation rejection. The products of Eisinger and Hefton contain 2 to 3% ATPase positive cells.

Morhenn et al, "Cultured Human Epidermal Cells Do Not Synthesize HLA-Dr", *The Journal of Investigative Dermatology*, 78:32–37 (1982) state that they obtained epidermal cell cultures grown on collagen gel or gelatin membranes free of the immune stimulatory antigen (HLA-Dr) and also free of Langerhans cells, following a culturing period of 7 days or longer. It is the present inventor's belief that the absence of HLA-Dr immunogens in Morhenn's product is due to a combination of culturing parameters, probably including the use of the collagen or gelatin substrate and not due solely to the duration of culturing. The present inventor has carried out culturing of epidermal cells for lengths of time of the same order as Morhenn et al and has found the HLA-Dr transplantation immunogens to be present. Furthermore, Morhenn et al (1) state that their cultured epidermal cells include some ATPase positive cells, which would be expected to be Langerhans cells, but if not could be a type of nonLangerhans dendritic cell possessing some immunocompetence, and (2) do not describe a process for producing an integral self-supporting sheet consisting of epidermal cells. The composite structure of Morhenn, including the collagen or gelatin substrate, would in itself be poorly suitable as a skin graft.

Earlier work of the present inventor has been abstracted by Hefton et al, "Guinea Pig Epidermal Cell Cultures: Development of Confluent Sheets and Their Transplantation," *Federal Proceedings*, Volume 39:376 (1980) where transplantation was onto syngenetic animals and by Hefton et al, "Human Epidermal Cells No Longer Stimulate Allogeneic Lymphocytes after Growth in Culture," *J. of Investigative Dermatology*, 5 Volume 76:308 (1981) where the cultured cell population still contained a low percentage of cells expressing HLA-Dr antigens.

SUMMARY OF THE INVENTION

Therefore, it is an object of the present invention to provide an epidermal sheet formed of confluent or associated human epidermal cells, useful as a skin graft.

Another object of the present invention is to provide an integral, self-supporting epidermal sheet formed of essentially one or more layers of ATPase negative human epidermal cells.

Still another object of the present invention is to provide an integral, self-supporting epidermal sheet formed essentially of one or more layers of ATPase negative human epidermal cells, which cells do not exhibit HLA-Dr immune stimulatory antigens.

A further object of the present invention is to provide an epidermal sheet usable as an allograft or homograft, that is for non-donor-related patients.

Another object of the present invention is to provide processes for culturing human epidermal cells to produce integral, self-supporting sheets of one or more layers of human epidermal cells, which sheets are essentially free of both ATPase positive cells and other cells which contain transplantation immune competent antigens.

Still another object of the present invention is to provide processes for treating burn victims or other patients needing skin grafts in which an epidermal sheet as disclosed herein is applied to affected areas. Other uses for the epidermal sheet of the present invention will be apparent to the skilled artisan, some of which will be discussed hereinbelow.

In accordance with the present invention, there is provided a process for growing human epidermal cells in vitro in the absence of dermal components to form an integral confluent, self-supporting sheet of one or more layers of pure human epidermis free of immune-competent cells, wherein dissociated epidermal cells are treated in a manner enabling selective removal of essentially all of the immune-competent cells prior to tissue growth. In one embodiment of the invention, the cells are treated enzymatically to disrupt essentially all immune-competent cells, including the cells exhibiting HLA-Dr antigens and including all ATPase-positive cells. In another embodiment, the dissociated epidermal cells are treated with a protein material which selectively attaches to the immune-competent cells, including the ATPase-positive cells.

More particularly, in accordance with a preferred aspect of the above-disclosed first process embodiment of the present invention, a single cell suspension of epidermal cells containing ATPase-positive cells and/or other immune stimulatory cells is incubated in the presence of deoxyribonuclease (DNase), the intact cells are collected and then the collected cells are cultured to yield a self-supporting sheet of pure epidermal tissue.

In a preferred aspect of the above-disclosed second process embodiment of the present invention, a single cell suspension of epidermal cells containing ATPase-positive cells and/or other immune stimulatory cells is incubated in the presence of tobacco glycoprotein (TGP), the epidermal cells to which the TGP does not attach are collected, and the collected cells are cultured to yield a self-supporting sheet of pure epidermal tissue.

In preferred embodiments of the present invention, the collected cells are grown in a plastic flask in a tissue culture medium having a pH of about 6.5 to 7.2.

DETAILED DESCRIPTION OF THE INVENTION

In the practice of the present invention, human skin is obtained from a suitable donor such as cadavers, unrelated to possible skin graft recipients. Therefore, the skin graft products of this invention can be produced in quantity, packaged and stored under conditions providing availability upon need without concern as to immune-rejection by the recipient.

First of all, turning to the epidermal sheet production process, epidermis of human skin can be separated from the dermis using prior art techniques. In general, it is known to incubate skin specimens in trypsin-containing media, followed by mechanical separation of the epidermis from the dermis. However, in a procedure recommended herein, the concentration of trypsin is elevated beyond the levels believed to be taught in the prior art. The aforementioned Eisinger and Hefton procedure and Morhenn et al article disclose the use of 0.25% and 0.3% trypsin solutions to facilitate separation of dermis from epidermis. At this time, the present inventor's preferred procedure employs incubation in a 0.5% trypsin solution. The recommended step is to incubate at about 32 to 40° C., preferably about 37° C., for about 45 to 120 minutes, preferably about 90 minutes, in about a 0.3 to 0.75% trypsin solution, preferably about 0.5% trypsin.

Following separation of dermis from epidermis, the epidermis is dissociated into essentially single cells to form a single cell suspension of epidermal cells in a liquid medium. Concomitantly with dissociation, or thereafter but prior to significant tissue sheet growth, the epidermal cells are treated to enable selective removal of the immune-competent cells from the overall epidermal cell population.

As disclosed hereinabove, the present invention comprises two process techniques to enable removal of the ATPase-positive and other immune-competent cells from remaining epidermal cells. Although these two broad embodiments are disclosed herein for practice one to the exclusion of the other, it is believed that without undue experimentation, a combined simultaneous or sequential process utilizing both techniques could be operable.

The preferred process embodiment at this time to enable separation of the undesirable ATPase-positive and other immune-competent cells from the remainder involves the incubation of the epidermal single cells in DNase. The single cells can be conveniently dispersed in an aqueous solution of about 0.1 to 0.6% DNase, and held therein at a temperature of about 18 to 37° C., preferably about 20 to 25° C. for about 10 to 60 minutes, with vigorous agitation such as by stirring with a sterile glass rod. The above suggested DNase concentrations are based on use of D 0751 (DN-100) DNase available from Sigma (St. Louis, MO), having an activity of approximately 1,4000 Kunitz units per milligram protein. Adjustment in DNase concentration should be made based on activity of the DNase employed, through routine calculation and experimentation. Conventional analytical techniques such as immunofluorescent staining for HLA-Dr antigens, ultrastructural identification of Langerhans cells, ATPase staining and the like can be employed to monitor the DNase incubation step. It is expected that the concentration of DNase toward the lower range above defined would involve longer incubation times than the employment of higher DNase concentrations. At the present time, the recommended DNase concentration is approximately 0.5%. The DNase can be dissolved in an isotonic medium, such as MEM, PBS, normal saline, etc. The present inventor has found that the use of a 0.025% DNase incubation for about 30 minutes at about 21° C. does leave about 0.5% cells bearing HLA-Dr antigen, which cells should stimulate allogenic T cells, after two days of culturing, as compared to 5 to 7% of said cells prior to culturing. It is noted that the ability of epidermal cells to stimulate the proliferation of allogenic T-lymphocytes in a MSLR (mixed skin cell lymphocyte reaction) can serve as one measure of histoincompatibility.

From the above, it is possible to treat the suspension of single epidermal cells with DNase under conditions which do not remove all of the ATPase-positive and other immunostimulatory cells, but to reduce the level to such an extent that the remaining cells dissiPate during culturing. It is preferred that the treatment with DNase be under conditions which remove all of the ATPase-positive and other immune stimulatory cells prior to cell culturing.

The second technique for removal of the undesirable ATPase positive and other immune stimulatory cells involves contacting the epidermal single cells with a glycoprotein which selectively attaches to the undesirable immune-competent cells. Simultaneously with or following attachment, the cells having the glycoprotein attached thereto are separated from the desired (non immune stimulatory) cells, which cells do not associate with the glycoprotein. At the present time, the preferred glycoprotein is tobacco glycoprotein (TGP), which is described in detail by Becker et al, "Tobacco, Cocoa, Coffee, and Ragweed: Cross-Reacting Allergens That Activate Factor-XII-Dependent Pathways," *Blood*, Volume 58, No. 5, p. 861 (1981). It is expected that other protein materials, including at least some of those which are structurally related to TGP, such as rutin, cocoa antigen, etc., could be substituted for TGP in the present invention by routine experimentation. A suggested process which has been employed involving the use of TGP is to attach the TGP to a solid phase, such as glass beads or a Sepharose column, bring the solid phase into contact with the single cell suspension, such as by passing the suspension through a TGP-Sepharose column, and recovering the cells remaining dissociated from the solid phase (affinity chromatography).

Returning to the use of the DNase, following the incubation treatment, filtration can be carried out using a filtering medium allowing passage of whole cells, while retaining clumps of debris larger than the single cells. The cells which are disrupted by the enzyme and/or fragments thereof clump together into units larger than single cells. For example, a sterile gauze filter can be employed. Thereafter, the cells can be collected and concentrated by centrifugation, for example for 10 minutes at 200 g.

Following the removal of the undesirable ATPase-positive and other immune-competent cells, the remaining epidermal cells are grown in a tissue culture medium. Although conventional prior art tissue growth mediums and processes such as those of Eisinger and Hefton, disclosed above, can be employed at this stage, it has been found that tissue growth increases where the pH of the culture medium is controlled to be about pH 6.5 to 7.2. The recommended tissue culture growth conditions at this time are to utilize a temperature of around 37° C., atmosphere of 100% humidity, a cell culture medium containing about 20% fetal calf serum, with the cells being seeded into plastic tissue culture vessels to a final density of about $10^5$ to $10^8$ cells per ml of culture medium. One milliliter of culture medium is added to each flask per 5 cm$^2$ of surface area of the flask covered by the culture medium. Thus, the seeding density can be expressed as $10^5$ to $10^8$ cells per 5 cm$^2$ of flask surface area.

Subculturing can be carried out for about 7 to 21 days, depending upon the thickness of tissue sheet desired. At times, an epidermal sheet consisting of a single or monolayer of epidermal cells could prove useful, while in most cases involving the formation of grafting products, a multi-layered integral epidermal sheet would be preferred. A single layer product or a product having several layers of cells will be used depending on wound depth, wound size and the like factors.

The epidermal sheet attaches to the plastic culture flask. To remove the epidermal sheet, an enzyme which preferentially acts at the tissue sheet-plastic interface can be employed, for example dispase in a concentration of about 0.1 to 1.0%. The dispase concentration will depend on the specific activity of the enzyme, the dispase used herein having a specific activity of 0.5 units per milligram lyophilized enzyme. Routine experimentation would indicate the correct amount of the enzyme to be used.

A transfer member, such as the dermal side of pig skin, a collagen sponge, a sheet of polyvinylidene polymer, polyester or hydrogel, or Vaseline-impregnated gauze, can be used to transfer the epidermal sheet from the plastic growth flask. The epidermal sheet is floated to such a transfer member for removal or floated directly to the area of application, to, for example, an afflicted area on a burn patient.

As discussed above, a notable advantage of the present invention is the provision of mono- or multi-layered epidermal sheets consisting of human epidermal cells which do not contain immune stimulatory antigens. As used herein, the term "essentially free of immune-competent cells" means that the level of immune-competent cells is so low that immunorejection does not occur when the tissue is used as a skin graft for non-related recipients. Similarly, the term "essentially free of ATPase-positive cells" means that the level of ATPase positive cells is below that causing rejection when the tissue is used as a skin graft for an unrelated recipient. The Examples presented hereinbelow provided epidermal cell tissues which did not contain any immune-competent cells as tested by immunofluorescent staining and by ATPase staining. Thus, transplantation can be carried out for burn patients who are unrelated to the donor, which can be a cadaver. Of course, other uses will exist for the epidermal sheets provided by the present invention, such as for drug testing and the like, i.e., testing of various materials such as shampoos and cosmetics which contact the skin.

The following non-limiting examples illustrate the embodiments of the present invention.

EXAMPLE 1

Partial-thickness pieces of skin were removed with a keratome and immersed in Eagle's minimum essential medium at 4° C. (MEM) (Grand Island Biological Co., Grand Island, N.Y.) with 1,000 U penicillin/ml, 1,000 mcg streptomycin/ml, 25 mcg Fungizone/ml and 10% Fetal Bovine Serum (FBS). The skin was then cut into 5 mm$^2$ pieces and incubated in a 0.5% trypsin (1:250, Difco, Detroit, MI) solution in phosphate buffered saline (PBS) (GIBCO) for 90 minutes at 37° C.

Following this incubation the epidermal layers were mechanically separated from the underlying dermis and dispersed to single cells in 0.5% DNase (D0751 (DN-100), Sigma, St. Louis, MO) in PBS and held in the DNase with vigorous agitation at room temperature for about 30 minutes. After filtration through sterile gauze, the cells were collected by centrifugation (10 minutes, 200 g) and resuspended in complete medium (CM: MEM plus 2 mM l-glutamine (GIBCO), 20% FBS, 100 U penicillin/ml, 100 mcg streptomycin/ml, 2.5 mcg Fungizone/ml and 0.1 mM hydrocortisone (Merck, Sharp ; and Dohme, West Point, PA) at pH 5.8 to 6.0. The viability of cells prepared in this manner was 90 to 95% by trypan blue dye exclusion. Cells were seeded into plastic tissue culture flasks at a final density of $2 \times 10^5$ to $10^8$ cells per ml of culture medium. The cultures were incubated at 37° C. in 100% humidity in a 95% air/5% CO$_2$ environment. The medium was changed every three days and the cultures became confluent after 14 to 21 days. The cultured epidermal cells may be removed from the tissue culture flask any time after confluency, for example after 3 to 4 weeks in this particular instance. Prior to the removal from the flasks, the cells were incubated in MEM without FBS for 24 hours.

EXAMPLE 2

Partial-thickness pieces of skin were removed with a keratome and immersed in Eagle's minimum essential medium at 4° C. (MEM) (Grand Island Biological Co., Grand Island, NY) with 1,000 U penicillin/ml, 25 mcg Fungizone/ml and 10% Fetal Bovine Serum (FBS). The skin was then cut into 5 mm² pieces and incubated in a 0.5% trypsin (1:250, Difco, Detroit, MI) solution in phosphate buffered saline (PBS) (GIBCO) for 90 minutes at 37° C. The cells were collected and transferred to a PBS solution.

Tobacco glycoprotein (TGP) (or rutin conjugated with bovine serum albumin (rutin-BSA)) was isolated according to the procedures of Becker et al. TGP, or rutin-BSA, was then coupled to Sepharose-4B, packed into a column (1.5×20 cm) and washed with MEM at room temperature. The column was equilibrated with PBS solution. The single epidermal cell suspension was applied to the column and MEM was added to wash the keratinocytes into the collected effluent while the immune-competent cells adhered to the gylcoprotein-coated beads.

After passage through the column the cells were collected by centrifugation (10 minutes, 200 g) and resuspended in complete medium (C: MEM plus 2 mM l-glutamine (GIBCO), 20% FBS, 100 U penicillin/ml, 100 mcg streptomycin/ml, 2.5 mcg Fungizone/ml and 0.1 mM hydrocortisone (Merck, Sharp and Dohme, West Point, PA) at pH 5.8 to 6.0. The viability of cells prepared in this manner was 90 to 95% by trypan blue dye exclusion. Cells were seeded into plastic tissue culture flasks at a final density of $10^5$ to $10^8$ cells per ml of culture medium. The cultures were incubated at 37° C. in 100% humidity in a 95% air/5% $CO_2$ environment. The medium was changed every three days and the cultures became confluent after 14 to 21 days. The cultured epidermal cells may be removed from the tissue culture flask at any time after confluency with a neutral protease such as dispase.

The absence of immune competent cells was determined by two testing procedures (the cell population can be tested as single cell suspensions prior to sheet growth), with the cell population of the present invention containing zero per cent immune competent cells per both testing procedures.

ATPase Staining

In this method cultured cells are fixed in a 6% solution of cold neutral formalin. The cells are then incubated in 5 ml of 1.25% sodium glycerophosphate in 0.2 M tris buffer mixed with 30 ml 0.2% lead nitrate and 5 ml distilled water for 180 minutes at 37° C. After the incubation the cultured cells are washed in tap water and dipped in dilute ammonium sulfide for several minutes. The preparations are covered with glycerin prior to observation by light microscopy. The cells containing ATPase activity are revealed by black deposits of lead sulfide.

Immunofluorescent Staining

Cell suspensions containing $10^6$ cells were washed twice in phosphate buffered saline containing 2% bovine serum albumin (PBS-BSA) (Pentex) and 0.1% sodium azide. The cells were collected by centrifugation (200 g, 10 minutes) and resuspended in 20 microliters of commercially available anti-Dr serum (1:100 dilution) and incubated for 30 minutes at 4° C. After this incubation period, the cells were washed twice in PBS-BSA and collected by centrifugation (200 g, 10 minutes). Antibody binding was visualized by incubating the cells with commercially available fluorescein isothiocyanate (FITC)-conjugated F(ab')$_2$ fragments from goat antiserum directed against rabbit IgG molecules for 30 minutes at 4° C. After this incubation period, the cells were washed twice with PBS-BSA and collected by centrifugation (200 g 10 minutes). The cell pellets were resuspended in a small volume of PBS-BSA and then examined for fluorescence under a sealed cover slip with a Leitz Ortholux microscope equipped for incident illumination.

The pure epidermal cell sheets of the present invention have been used for grafting to non-related recipients. A procedure utilized has been to excise and cover second degree burn wounds with sterile Pigskin for 3 to 4 days to permit a bed of early granulation tissue to form. The pig skin is then removed and the cultured epidermal cell sheet placed on the granulation tissue with either side of the sheet facing the wound. The wound is then dressed with wet to wet moist dressings. The culture grafts may be redressed with occlusive or semi-occlusive dressings after the epidermal cells have adhered 24 to 48 hours after transplanation. The grafted area healed similar to second degree burn areas grafted with conventional split-thickness autografts, without any indication of rejection.

All percentages herein are weight by volume.

Other uses for the products of the present invention will be apparent to the skilled artisan, for example, for transplantation to patients undergoing cosmetic surgery or surgical oncology, patients having external wounds other than burn wounds, and the like. Other variations of the invention will be recognized by the skilled artisan, including modifications in the culturing procedures disclosed herein, without departing from the spirit and scope of the invention.

What is claimed is:

1. A process of treating a patient needing a skin transplant which comprises applying to afflicted areas an epidermal sheet produced by a process comprising treating a subpopulation of dissociated human epidermal cells with DNas in an amoutn sufficient to segregate immune competent cells from non-immune competent cells, thereafter recovering the non-immune competent cells as single cells, and growing an integral, self-supporting sheet of non-immune competent epidermal cells from said sub-population of cells.

2. The process of claim 1 wherein the sub-population of cells consists of cells which do not express HLA-Dr antigen.

3. The process of claim 1 wherein the sheet is grown at a pH of about 6.5 to 7.2.

4. The process of claim 1 wherein the sheet of epidermal cells attaches to a tissue culture vessel and the sheet is detached for the vessel by treating with a neutral protease.

5. The process of claim 1 wherein the dissociation of cells is aided by incubation of the skin in a 0.3 to 0.75% trypsin solution.

6. The process of claim 1 wherein the afflicted areas are burn wounds.

7. A process of treating a patient needing a skin transplant which comprises applying to afflicted areas a self-supporting epidermal sheet grown in tissue culture and consisting of essentially non-immune competent human epidermal cells being essentially free of immune competent cells.

8. The process of claim 7 wherein the tissue culture is carried out at a pH of about 6.5 to 7.2.

9. The process of claim 8 wherein the tissue culture is seeded in a medium at a density of $10^5$ to $10^8$ cells per milliliter.

10. The process of claim 7 wherein the afflicted areas are burn wounds.

* * * * *